(12) United States Patent
Noecker et al.

(10) Patent No.: US 7,402,181 B2
(45) Date of Patent: Jul. 22, 2008

(54) PRE-TREATMENT COMPOSITION FOR COLOURING HAIR

(75) Inventors: Bernd Noecker, Ober-Ramstadt (DE); Fariba Ghiasi, Frankfurt (DE)

(73) Assignee: KPSS - KAO Professional Salon Services GmbH, Darmstadt (DE)

( * ) Notice: Subject to any disclaimer, the term of this patent is extended or adjusted under 35 U.S.C. 154(b) by 306 days.

(21) Appl. No.: 10/862,600

(22) Filed: Jun. 7, 2004

(65) Prior Publication Data

US 2004/0216248 A1   Nov. 4, 2004

(30) Foreign Application Priority Data

Apr. 9, 2003   (EP) ................ 03 008 219

(51) Int. Cl.
C09B 62/00 (2006.01)
A61Q 5/10 (2006.01)

(52) U.S. Cl. ............... 8/542; 8/552; 8/554; 8/581; 424/70.2; 424/70.122; 132/202; 132/208

(58) Field of Classification Search ............... 424/70.2, 424/70.122; 8/542, 552, 554, 581; 132/202, 132/208

See application file for complete search history.

(56) References Cited

U.S. PATENT DOCUMENTS

| 5,618,525 | A | * | 4/1997 | Bunning ............... 424/70.122 |
| 6,217,855 | B1 | * | 4/2001 | Itou et al. ............... 424/70.2 |
| 2003/0126692 | A1 | * | 7/2003 | Devin-Baudoin et al. ...... 8/405 |

FOREIGN PATENT DOCUMENTS

| DE | 30 30 119 A1 | 2/1982 |
| EP | 0 640 643 A2 | 3/1995 |
| EP | 1 312 341 A2 | 5/2003 |
| GB | 2 173 515 A | 10/1986 |

OTHER PUBLICATIONS

Stic Search Repor Jul. 27, 2006.*
European Search Report for application No. EP 03 00 8219 dated Sep. 29, 2003.

* cited by examiner

Primary Examiner—Eisa B Elhilo

(57) ABSTRACT

This invention relates to a pre-treatment composition comprising at least one organopolysiloxane especially polysilicone-9 and to a process for application of the said composition, which has an acidic pH and is applied to hair, especially damaged hair, prior to hair colouration in order to improve the color intensity and at the same time to achieve durable hair color. pH of the pre-treatment compositions is from 2 to 7.

13 Claims, No Drawings

PRE-TREATMENT COMPOSITION FOR COLOURING HAIR

FIELD OF THE INVENTION

The present invention relates to a acidic pre-treatment composition comprising at least one organopolysiloxane and, to a coloration process using the said composition, which is applied, especially to damaged hair, prior to colouration in order to improve the colour intensity, evenness and at the same time achieving durable colour.

BACKGROUND OF THE INVENTION

Hair colouring is a common practice for ages. Oxidative colouration has been widely used for achieving durable, brilliant hair colour. Direct dyes, either of cationic or of anionic character, have also found their applications for colouring hair.

In practice, number of difficulties are observed when colouring human hair. One of them is variation in resulting hair colour with physical status of the hair. Good colouring performance is usually obtained with healthy, natural hair, whereas the colouring performance is not always found to be satisfactory in cases of damaged, chemically processed hair and especially with those of bleached hair. The reason underlying in performance difference may be that, penetration of the dyestuffs is varied with the degree of damages previously caused to the hair fibre. In daily hair colouring practice, this results in uneven colourations, colours lacking brilliance and durability.

SUMMARY OF THE INVENTION

In order to solve the aforementioned problem, it has surprisingly been found out that before carrying out colouration either oxidative or with direct dyes, application of a acidic pre-treatment composition comprising at least one organopolysiloxane resulted in homogeneous penetration and/or binding of dyestuffs into or onto hair. This leads to achieving intensive and even hair colourations. The colour so achieved has shown excellent durability at the same time. The pre-treatment composition described in the invention can be applied prior to hair colouration with either oxidative dyes or direct dyes.

DETAILED DESCRIPTION OF THE INVENTION

The pre-treatment composition is characterised in that
it has pH value from 2 to 7, preferably 2 to 6 and more preferably 2-5.5, and comprising
at least one organopolysiloxane as described with the following formula which is also disclosed in the application EP 640 643 A2

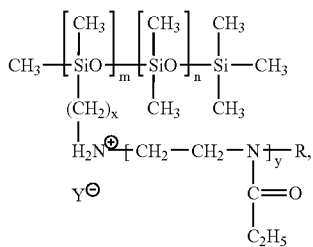

where m and n are numbers from 20 to 10,000, preferably from 50 to 7,000 and more preferably from 100 to 5,000, x is a number between 1 and 5 preferably 3, y is a number from 5 to 30, R is a C1-C12 alky or aryl group especially methyl, ethyl or benzyl group and Y is an anion such as ethylsulphate.

A preferred grafted polymer according to the formula has molecular weight from 50,000 to 500,000, preferably from 80,000 to 300,000, more preferably about 100,000 dalton wherein the molecular weight of the oxazoline segment is from 2,500 to 7,500, preferably 4,000 to 6,000 and especially about 5,000 dalton/segment and molar fraction is 20 monomer/molecule. The preferred Si contents is around 50% according to the molecular analysis.

The concentration of the organopolysiloxane grafted polymer in the pre-treatment composition is typically from 0.01 to 5% by weight, preferably from 0.01 to 3% by weight, more preferably from 0.01 to 2% by weight and most preferably 0.05-1% by weight, calculated to the total composition.

The process of colouring hair with the use of pre-treatment composition described here involves the following step.
1—Application of the pre-treatment composition and subsequently
2—Colouring hair with colouring agents containing either oxidative or direct dyes and
3—After a predetermined processing time the hair is rinsed off and shampooed at least once.

In this process, between the two steps, although it is not essential, hair may be towel dried or air dried or dried with an electrical drier. Hair may also be optionally rinsed off and with or without (towel) drying and/or drying with an electrical drier colouring process can be continued. When colouring agent is applied directly after application of the pre-treatment composition, an up to 5 minute processing time should be allowed before applying colouring agents.

It has further been found out that drying hair before colouration, with and/or without processing time after application of the pre-treatment, improves evenness of colour further, as no dilution of colouring agents takes place during the process.

It has also been found out that amount of pre-treatment applied to hair is an important parameter. Special attention must be paid to even application of pre-treatment onto hair so that hair is saturated with the pre-treatment composition. Typical amounts of 20-35 g are found to be satisfactory for medium length hair. This can also be expressed in a pre-treatment amount to hair ratio which should be in the range from 0.3:1 to 2:1 by weight and in any event typically in the range of 0.5:1 to 1:1.

For adjusting the pH of the said pre-treatment composition, following ingredients can be used: Organic acids such as citric acid, lactic acid, tartaric acid, malic acid, maleic acid, fumaric acid, levulinic acid, butyric acid and hydroxy butyric acids, valeric acid, oxalic acid, succinic acid, mandelic acid, glycolic acid, glucuronic acid, propionic acid, salicylic acid or acetic acid or inorganic acids such as hydrochloric acid, phosphoric acid, sulphuric acid, nitric acid. Concentration of the organic and/or inorganic acids or their mixtures should be adjusted in a way that pre-treatment composition so obtained has a pH value between 2 and 7, preferably 2-6 and more preferably 2-5.5. Typically concentration for acids can be 0.01-10% by weight, preferably 0.05-8% by weight, more preferably 0.1-8% by weight and most preferably 0.1-6% by weight calculated to the total composition. The pH of the pre-treatment composition can also be adjusted to the required pH by using alkaline solution such as sodium hydroxide, potassium hydroxide, ammonium hydroxide or their salts with those acids mentioned above in the case that at the selected acid concentration pH of the composition is lower than that of the aimed value.

The pre-treatment composition of this invention comprises optionally hair conditioning agents. Conditioning agents can be selected from oily substances, non-ionic substances, cationic amphiphilic ingredients, cationic polymers or their mixtures. Oily substances are selected from such as silicone oils either volatile or non-volatile, natural and synthetic oils. Among silicone oils those can be added to the pre-treatment composition include dimethicone, dimethiconol, polydimethylsiloxane, DC fluid ranges from Dow Corning, natural oils such as olive oil, almond oil, avocado oil, weizenkeim oil, ricinus oil and the synthetic oils, such as mineral oil.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula I or II, respectively,

   formula I

   formula II where $R_1$ and $R_2$ are independent from each other saturated, unsaturated or branched or non-branched alkyl chain with 7 to 21 C atoms and n is typically 2-100.

Pre-treatment composition can contain cationic amphiphilic conditioning ingredients according to the formula III, but not limited to.

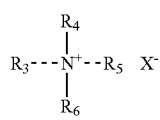

Formula III where $R_3$ is a saturated or unsaturated, branched or non-branched alkyl chain with 8-22 C atoms or

where $R_7$ is saturated or unsaturated, branched or non-branched alkyl chain with 7-21 C atoms and n has typical value of 1-4 or

where $R_8$ is saturated or unsaturated, branched or non-branched alkyl chain with 7-21 C atoms and n has typical value of 1-4, and $R_4$ is H or unsaturated or saturated, branched or non-branched alkyl chain with 1-22 C atoms or

or

where $R_7$, $R_8$ and n are same as above.

$R_5$ and $R_6$ are H or lower alkyl chain with 1 to 4 Carbon atoms, and X is typically chloride, bromide, methosulfate.

Typical examples of those ingredients are cetyl trimethly ammonium chloride, steartrimonium chloride, behentrimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate.

Pre-treatment composition can also contain cationic polymers as conditioning agents. Suitable polymers are those of cationc polymers best known with their CTFA category name Polyquaternium. Typical examples of those Polyquaternium 6, Polyquaternium 7, Polyquaternium 10, Polyquaternium 11, Polyquaternium 16, Polyquaternium 22, Polyquaternium 28 and Polyquaternium 37. It has been found out that especially those of cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride, are preferred ones. Furthermore, chitosan and chitin can also be included in the compositions as cationic natural polymers.

Typical concentration range for any of the conditioners mentioned above can be 0.01-5% by weight, preferably 0.03-2% by weight and more preferably 0.05-0.1% by weight calculated to the total composition.

The pre-treatment compositions may contain organic solvents such as ethanol, propanol, isopropanol, benzyl alcohol, benzyloxyethanol, alkylene carbonates such as ethylene carbonate and propylene carbonate, phenoxyethanol, butanol, isobutanol, cyclohexane, cyclohexanol, hexyleneglycol, ethylene glycol, butylenes glycol, propylene glycol, benzyl glycol, ethylene glycol monoethylether, ethylene glycol monobutyl ether, ethylene glycol monophenyl ether, 1-phenylethylalcohol, 2-phenylethylalcohol, o-methoxyphenol. Concentration of organic solvents in the pre-treatment composition can be in the range from 10 to 40% by weight, preferably 10 to 35% by weight, and more preferably 10 to 30% by weight calculated to the total composition.

Pre-treatment composition can be in the form of a solution, with either transparent, semitransparent or non-transparent milky appearance, gel type of preparation again with either transparent, semitransparent or non-transparent appearance, or an emulsion. The compositions can have viscosity values less than 40,000 mPa·s, preferably less than 20,000 mPa·s and more preferably less than 15,000 mPa·s and most preferably less than 10,000 mPa·s measured at 20° C. with Brookfield viscosimeter with, for example, Spindle 4 at 10 rpm. The viscosity values are read after 30 seconds from the start of the measurement. In the selection of the viscosity, special attention must be paid to the way of application and packaging to be used. In other words, for example, when a spray application is preferred, the viscosity of preparations must be low enough allowing spraying.

Pre-treatment composition can be packed into a bottle with a nozzle which enables easy application or with a spray device (pump spray) or with a pump which enables dispensing the composition in the form of liquid or foam (pump foamer). Composition may also be offered in an aerosol bottle from which the composition is dispensed as a foam. In the aerosol form, dispensing as a spray may also find its applications in the daily practice. In the case that aerosol form is preferred, suitable propellant gas or mixtures must be added to the composition to make dispensing in the preferred form possible.

For gel type preparations, compositions may contain nonionic polymers such as hydroxyethylcellulose, hydroxypropylclellulose, xanthan gum, xyloglucan, polyvinylalcohol, polyvinylpyrrolidone or their derivatives.

Anionic polymers may also be used as thickeners. Typical example of those is acrylate type of polymers know with the trade name Carbopol from Goodrich.

In the case that pre-treatment composition is an emulsion, the composition may then contain fatty alcohols with 12 to 22 carbon atoms and non-ionic emulsifier such as ethoxylated fatty alcohols with general formula (IV)

$$R_9(OCH_2CH_2)_nOH \quad \text{formula IV}$$

where R9 is saturated or unsaturated, branched or non-branched alkyl chain with 8-22 C atoms and n has typical value of 2-100.

Solubilizers may be added to the compositions especially when oily substances are chosen as conditioning agents. Typical solubilizers may be hydrogenated castor oil known with the trade mark Cremophor RH series from BASF, non-ionic surfactants, such as ethoxylated fatty alcohols, alkyl glucoside, or amphoteric surfactants such as betaine type i.e. cocamidopropyl betaine. Ethoxylated fatty alcohols such as Laureth-23 and as described above are also found to be suitable solubilizers. Typical concentration of the solubilizers can be in the range of 0.01-2% by weight, preferably 0.05-1% by weight.

Pre-treatment composition may contain additional cosmetic ingredients such as fragrance, preservative, sequestering agents, UV filters.

Following are the examples to illustrate the invention but are not to be interpreted as limiting it.

EXAMPLE 1

|  | % by weight |
| --- | --- |
| Polysilicone-9 | 0.30 |
| Ethanol | 10.0 |
| Benzylglycol | 2.5 |
| Butylene glycol | 2.0 |
| Laureth-23 | 0.4 |
| PEG-40 Hydrogenated castor oil | 0.4 |
| Behentrimonium chloride | 0.3 |
| Polyquaternium 10 | 0.2 |
| Lactic acid | 1.0 |
| Ammonium hydroxide | q.s. to adjust the pH to 4.5 |
| Fragrance, preservative | q.s. |
| Water | to 100 |

All ingredients are added to water one by one and dissolved, except fragrance which is mixed first with Cremophor RH 40 and aqueous solution of cetrimonium chloride and then added to the mixture. The composition so obtained is a solution with a viscosity less than 500 mPa·s. at 20° C. The composition can be provided in a bottle with an application nozzle Colouring Test:

Healthy and oxidatively bleached Caucasian hair (original colour is medium blond) tresses are prepared as hair samples for colouring tests. The tresses are bleached 3× with commercially available agents (Oxycure Platin from Goldwell GmbH). Elumen RR @ all (commercial product under the brand name Goldwell) is used as colouring agent in all tests unless otherwise stated. In each test run two tresses used and one as being control, coloured without pre-treatment (see below), and to the other first a pre-treatment composition as described above is applied. The applied amount of the pre-treatment solution is equal to the weight of the hair tress (1:1 ratio of pre-treatment: hair by weight). After drying tresses with and electical dryer, colouring agent is applied and processed for 20 minutes at 40° C., then rinsed off and dried with an electrical drier. Colour measurements are carried out with a commercial equipment (Minolta CR-200) in order to determine the difference in colour nature and intensity. Delta E values are calculated from the L, a and b values measured before and after colouration. Results are presented in Table I.

TABLE I

|  | Pre-treatment | Delta E |
| --- | --- | --- |
| Healthy hair | − | 57.0 |
|  | + | 58.5 |
| Bleached hair | − | 62.0 |
|  | + | 73.0 |

As can be seen from the delta E values, application of the pre-treatment on healthy, undamaged, hair has only a slight effect, whereas the effect is very much elevated on bleached, chemically damaged hair.

For testing the effect of amount of the pre-treatment composition applied to the hair, same as above oxidatively damaged hair tresses are taken and coloured in the same way as described above. In the process only the amount of applied pre-treatment is varied as 0.5, 1.0 (same as above) and 2.0 times of the weight of the hair tress. Colour measurements are carried out and delta E values are calculated in the same way as above. Results are presented in Table II.

TABLE II

| Pre-treatment:Hair ratio | Delta E |
| --- | --- |
| 0:1 | 62.0 |
| 0.5:1 | 72.6 |
| 1:1 | 73.0 |
| 2:1 | 73.5 |

The results show clearly that even at lower application amounts of pre-treatment (pre-treatment: hair ratio of 0.5:1) excellent colour intensity is achieved.

For testing durability, tresses coloured in the same way as described above with and without pre-treatment are subjected to a wash test. The wash test is carried out as placing the tresses in a 10% by weight solution of shampoo suitable for coloured hair (Definition Color and Highlight Shampoo, commercial product under the brand name Goldwell) and shaken in a water bath at 30° C. and at approximately 50 rpm for 15 minutes. The tresses are then taken out and rinsed with running water at around same temperature and after drying colour measurements are carried out. The delta E values are calculated by taking the L, a and b values before colouring the tress as a reference. The same procedure is repeated for the second time in the same way. This test is only carried out on chemically damaged hair tresses and with 2 different colours from the same brand commercially available, Goldwell.

TABLE III

|  | NB@5 | | RR@all | |
|  | Delta E | | | |
|  | without | with | without | with |
| --- | --- | --- | --- | --- |
| After colouring | 46 | 52 | 61 | 73 |
| 15 min shaking | 40.5 | 47.5 | 55 | 68.5 |
| 30 min shaking | 38 | 46 | 52 | 64.5 |

As results show clearly, not only the colour intensity but also the durability is very much enhanced by application of pre-treatment before colouring hair with acidic dyestuff containing colouring agents.

Similar results are as well obtained with the following examples when direct dyes containing colouring agents used. In addition, the effect is well observed with colouring agents consisting of oxidative dyes.

EXAMPLE 2

|  | % by weight |
| --- | --- |
| Polysilicone-9 | 0.60 |
| Ethanol | 20.0 |
| Benzylalcohol | 1.0 |
| Propylene glycol | 2.0 |
| Laureth-23 | 0.3 |
| PEG-40 Hydrogenated castor oil | 0.3 |
| Cetrimonium chloride | 0.2 |
| Polyquaternium 6 | 0.1 |
| Citric acid | 1.0 |
| Ammonium hydroxide | q.s. to adjust the pH to 4.0 |
| Fragrance, preservative | q.s. |
| Water | to 100 |

The composition is prepared in the same way as in the example 1.

The composition is tested with emulsion type (the emulsion base used is same as in the German patent DE 199 04 291 C2) of oxidative colourations with dye composition as follows (all values are % by weight calculated to the total composition).

| m-aminophenol | 0.2 |
| --- | --- |
| 2-Amino-4-hydroxyethylaminoanisol | 0.5 |
| 2,5-Diaminotoluolsulphate | 3.0 |
| Resorcin | 1.2 |

The emulsion composition containing the above oxidative dyestuff precursors, is mixed prior to application 1:1 with 6% hydrogen peroxide containing oxidising composition.

Similarly as above, using the same hair tresses the dyeing efficiency is tested with and without application of the pre-treatment composition on natural and oxidatively damaged hair. All measurements and colouring processes are carried out same as given for example 1. Certainly the colouring agent of the example 2 is mixed with oxidizing agent prior to application. The results are summarised in table IV.

TABLE IV

|  | Pre-treatment | Delta E |
| --- | --- | --- |
| Healthy hair | – | 30.2 |
|  | + | 32.0 |
| Bleached hair | – | 66.5 |
|  | + | 74.0 |

Similar to the results obtained in Example 1 with direct dyeing acidic dyes, the colouring intensity is increased slightly in the case of healthy hair and with the use of pre-treatment composition of Example 2 when oxidative colouring agents are used. The effect of the pre-treatment is well observed in the case of the damaged hair.

Similar results are as well observed with the following examples with colouring agents consisting of either direct dyes or oxidative dyes.

EXAMPLE 3

|  | % by weight |
| --- | --- |
| Polysilicone-9 | 0.80 |
| Ethanol | 20.0 |
| Benzylalcohol | 1.0 |
| Propylene glycol | 2.0 |
| Laureth-23 | 0.3 |
| PEG-40 Hydrogenated castor oil | 0.3 |
| Cetrimonium chloride | 0.2 |
| Polyquaternium 6 | 0.1 |
| Lactic acid | 1.0 |
| Ammonium hydroxide | q.s. to adjust the pH to 5.5 |
| Fragrance, preservative | q.s. |
| Water | to 100 |

The composition is prepared in the same way as in example 1.

EXAMPLE 4

|  | % by weight |
| --- | --- |
| Polysilicone-9 | 0.80 |
| Ethanol | 20.0 |
| Benzylalcohol | 1.0 |
| Propylene glycol | 2.0 |
| Laureth-23 | 0.3 |
| PEG-40 Hydrogenated castor oil | 0.3 |
| Cetrimonium chloride | 0.2 |
| Polyquaternium 16 | 0.1 |
| Lactic acid | 3.0 |
| Malic acid | 2.0 |
| Ammonium hydroxide | q.s. to adjust the pH to 3.0 |
| Fragrance, preservative | q.s. |
| Water | to 100 |

The composition is prepared in the same way as in example 1.

The invention claimed is:

1. Pre-treatment composition to be used prior to hair colouration characterised in that it has a pH in the range from 2 to 7 and comprises Polysilicone-9.

2. Pre-treatment composition according to claim 1, characterised in that it contains Polysilicone-9 at a concentration of 0.01-5% by weight calculated to the total composition.

3. Pre-treatment composition according to claim 1, characterised in that it comprises organic and/or inorganic acids or their mixtures at a concentration of 0.01-10% by weight calculated to the total composition.

4. Pre-treatment composition according to claim 1, characterised in that it comprises at least one physiologically compatible hair conditioning agent selected from oily substances, non-ionic substances, cationic amphiphilic compounds, cationic polymers or their mixtures at a concentration of 0.01 to 5% by weight calculated to the total composition.

5. Pre-treatment composition according to claim 1, comprises organic solvents at a concentration of 10-40% by weight calculated to the total composition.

6. Pre-treatment composition according to claim 1, wherein the composition has a viscosity of less than 40,000 mPa·s.

7. Pre-treatment composition according to claim 6, wherein the composition has a viscosity of less than 20,000 mPa·s.

8. Pre-treatment composition according to claim 7, wherein the composition has a viscosity of less than 15,000 mPa·s.

9. Pre-treatment composition according to claim 8, wherein the composition has a viscosity of less than 10,000 mPa·s.

10. Process for colouring hair characterised in that pre-treatment composition according to claim 1 is applied first to the hair and optionally left on the hair up to 5 minutes then colouring agent consisting of either oxidative dyes or direct dyes is applied and after a predetermined processing time the hair is rinsed of and shampooed at least once.

11. Process according to claim 10 characterised in that hair is towel dried or air dried or dried with an electrical drier after application of said pre-treatment composition and subsequently colouring agent consisting of either oxidative or direct dyes is applied.

12. Process according to claim 10 characterised in that applied amount of pre-treatment to hair ratio is in the range from 0.3:1 to 2:1 by weight.

13. Process according to claim 12 characterised in that applied amount of pre-treatment to hair ratio is in the range from 0.5:1 to 1:1 by weight.

* * * * *